(12) United States Patent
Dahl et al.

(10) Patent No.: US 7,691,891 B2
(45) Date of Patent: Apr. 6, 2010

(54) DIPHENYLUREA DERIVATIVES AND THEIR USE AS CHLORIDE CHANNEL BLOCKERS

(75) Inventors: Bjarne H. Dahl, Ballerup (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 773 days.

(21) Appl. No.: 10/561,189

(22) PCT Filed: Jun. 15, 2004

(86) PCT No.: PCT/EP2004/051111

§ 371 (c)(1),
(2), (4) Date: Dec. 16, 2005

(87) PCT Pub. No.: WO2004/111017

PCT Pub. Date: Dec. 23, 2004

(65) Prior Publication Data

US 2006/0178413 A1 Aug. 10, 2006

(30) Foreign Application Priority Data

Jun. 17, 2003 (DK) .............................. 2003 00898

(51) Int. Cl.
*A61K 31/41* (2006.01)
*C07D 257/00* (2006.01)

(52) U.S. Cl. ....................................... 514/381; 548/250
(58) Field of Classification Search .................. 514/381; 548/250
See application file for complete search history.

(56) References Cited

U.S. PATENT DOCUMENTS

| 6,297,261 | B1 * | 10/2001 | Christophersen et al. ..... 514/340 |
| 6,696,475 | B2 * | 2/2004 | Dahl et al. .................. 514/381 |
| 2002/0037905 | A1 | 3/2002 | Dahl et al. |
| 2006/0058395 | A1 * | 3/2006 | Lichtenberg et al. ........ 514/579 |
| 2006/0160856 | A1 * | 7/2006 | Dahl et al. .................. 514/326 |
| 2007/0293553 | A1 * | 12/2007 | Dahl et al. .................. 514/381 |

FOREIGN PATENT DOCUMENTS

| WO | WO-97/45400 A1 | 12/1997 |
| WO | WO-98/47879 A1 | 10/1998 |
| WO | WO-00/20378 A1 | 4/2000 |
| WO | WO-00/24707 A1 | 5/2000 |
| WO | WO-2004/012733 A | 2/2004 |
| WO | WO-2004/022529 A | 3/2004 |

OTHER PUBLICATIONS

Phillis et al., Brain Research, 780, 1998, 352-355, especially p. 355.*
Patani et al., Chem Rev., 1996, vol. 96, No. 8, pp. 3147-3176, especially p. 3149.*

* cited by examiner

*Primary Examiner*—Golam M. M. Shameem
*Assistant Examiner*—Susannah Chung
(74) *Attorney, Agent, or Firm*—Birch, Stewart, Kolasch & Birch, LLP

(57) ABSTRACT

The present invention relates to novel diphenylurea derivatives useful as chloride channel blockers. In other aspects the invention relates to the use of these compounds in a method for therapy, and to pharmaceutical compositions comprising the compounds of the invention.

5 Claims, No Drawings

DIPHENYLUREA DERIVATIVES AND THEIR USE AS CHLORIDE CHANNEL BLOCKERS

TECHNICAL FIELD

The present invention relates to novel diphenylurea derivatives useful as chloride channel blockers.

In other aspects the invention relates to the use of these compounds in a method for therapy, and to pharmaceutical compositions comprising the compounds of the invention.

BACKGROUND ART

Chloride channels serve a wide variety of specific cellular functions and contribute to the normal function of i.a. skeletal and smooth muscle cells. Chloride channels are probably found in every cell, from bacteria to mammals. Their physiological tasks range from cell volume regulation to stabilization of the membrane potential, transepithelial or transcellular transport and acidification of intracellular organelles.

WO 97/45400, WO 98/47879, WO 00/20378 and WO 00/24707 (all NeuroSearch ANS) describe compounds, such as substituted phenyl derivatives, active as chloride channel blockers.

However, there is a continued strong need to provide compounds with an optimized pharmacological profile. Furthermore, there is a strong need to find effective compounds without unwanted side effects associated with older compounds.

SUMMARY OF THE INVENTION

It is an object of the invention to provide novel compounds which act as chloride channel blockers.

A further object of the invention is the provision of compounds with a better selectivity. A still further object is the provision of compounds with a better potency.

A further object of the invention is the provision of compounds that act on cell or tissue specific chloride channels. A still further object is the provision of compounds that act on specific groups or subtypes of chloride channels.

A still further object is the provision of compound with more optimal pharmacodynamic properties such as kinetic behaviour, bioavailability, solubility and efficacy.

In its first aspect, the invention provides a compound of general formula I,

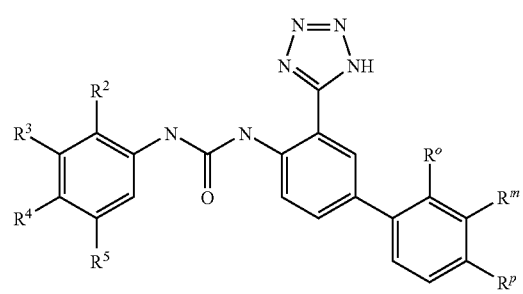

or a pharmaceutically acceptable salt thereof, wherein $R^o$, $R^m$, $R^p$, $R^2$, $R^3$, $R^4$ and $R^5$ are as defined below.

In its second aspect, the invention provides a pharmaceutical composition, comprising a therapeutically effective amount of a compound of the invention, or a pharmaceutically acceptable salt thereof, together with at least one pharmaceutically acceptable carrier, excipient or diluent.

In a further aspect, the invention provides the use of a compound of the invention, or a pharmaceutically acceptable salt thereof, for the manufacture of a pharmaceutical composition for the treatment, prevention or alleviation of a disease or a disorder or a condition of a mammal, including a human, which disease, disorder or condition is responsive to the blockade of chloride channels.

In a still further aspect, the invention relates to a method for treatment, prevention or alleviation of a disease or a disorder or a condition of a living animal body, including a human, which disorder, disease or condition is responsive to responsive to blockade of chloride channels, which method comprises the step of administering to such a living animal body in need thereof a therapeutically effective amount of a compound of the invention, or a pharmaceutically acceptable salt thereof.

Other objects of the invention will be apparent to the person skilled in the art from the following detailed description and examples.

DETAILED DISCLOSURE OF THE INVENTION

Diphenylurea Derivatives

In its first aspect, the invention provides a compound of general formula I,

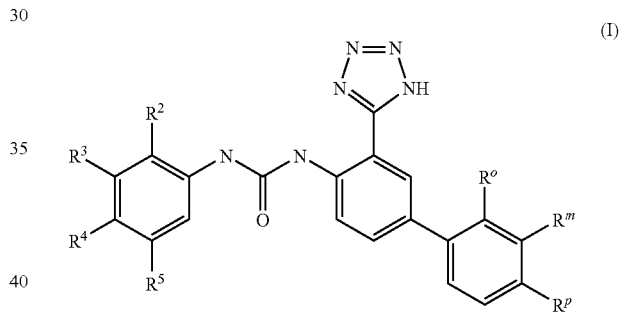

or a pharmaceutically acceptable salt thereof, wherein $R^o$, $R^m$ and $R^p$ independently of each other represent hydrogen, halo, trifluoromethyl, trifluoromethoxy, alkyl or alkoxy;

with the proviso that not all three of $R^o$, $R^m$ and $R^p$ represent hydrogen;

$R^2$, $R^3$, $R^4$ and $R^5$ independently of each other represent hydrogen, halo, trifluoromethyl, trifluoromethoxy, alkyl or alkoxy;

with the proviso that the compound is not N-(3-Trifluoromethyl-phenyl)-N'-[3-(1H-tetrazol-5-yl)-4'-trifluoromethyl-biphenyl-4-yl]-urea.

In one embodiment of the compound of general formula I, $R^o$ represents hydrogen; $R^m$ represents hydrogen; and $R^p$ represents halo, trifluoromethyl, trifluoromethoxy, alkyl or alkoxy. In a special embodiment, $R^p$ represents halo, such as chloro or fluoro, or bromo. In a further embodiment, $R^p$ represents trifluoromethyl. In a still further embodiment, $R^p$ represents trifluoromethoxy. In a further embodiment, $R^p$ represents alkyl, such as methyl. In a still further embodiment, $R^p$ represents alkoxy, such as methoxy.

In a further embodiment of the compound of general formula I, $R^o$ represents hydrogen; $R^p$ represents hydrogen; and R''' represents halo, trifluoromethyl, trifluoromethoxy, alkyl or alkoxy. In a special embodiment, R''' represents trifluoromethyl.

In a further embodiment of the compound of general formula I, $R^3$, $R^4$ and $R^5$ represent hydrogen; and $R^2$ represents halo, trifluoromethyl, trifluoromethoxy, alkyl or alkoxy. In a special embodiment, $R^2$ represents halo, such as chloro, fluoro or bromo. In a further embodiment, $R^2$ represents trifluoromethyl.

In a still further embodiment of the compound of general formula I, $R^2$, $R^4$ and $R^5$ represent hydrogen; and $R^3$ represents halo, trifluoromethyl, trifluoromethoxy, alkyl or alkoxy. In a special embodiment, $R^3$ represents trifluoromethyl. In a further embodiment, $R^3$ represents halo, such as bromo.

In a further embodiment of the compound of general formula I, $R^2$, $R^3$ and $R^5$ represent hydrogen; and $R^4$ represents halo, trifluoromethyl, trifluoromethoxy, alkyl or alkoxy. In a special embodiment, $R^4$ represents halo, such as chloro.

In a still further embodiment of the compound of general formula I, two of $R^2$, $R^3$, $R^4$ and $R^5$ represent hydrogen, and the other two of $R^2$, $R^3$, $R^4$ and $R^5$ independently of each other represent halo, trifluoromethyl, trifluoromethoxy, alkyl or alkoxy.

In a still further embodiment of the compound of general formula I, $R^2$ and $R^5$ represent hydrogen; and $R^3$ and $R^4$ independently of each other represent halo, trifluoromethyl, trifluoromethoxy, alkyl or alkoxy. In a special embodiment, $R^3$ represents trifluoromethyl. In a further embodiment, $R^4$ represents halo, such as chloro or fluoro. In a still further embodiment, $R^3$ represents trifluoromethyl and $R^4$ represents chloro. In a further embodiment, $R^3$ represents trifluoromethyl and $R^4$ represents fluoro.

In a still further embodiment of the compound of general formula I, $R^2$ and $R^4$ represent hydrogen; and $R^3$ and $R^5$ independently of each other represent halo, trifluoromethyl, trifluoromethoxy, alkyl or alkoxy. In a special embodiment, $R^3$ represents trifluoromethyl. In a further embodiment, $R^3$ represents halo, such as chloro or fluoro. In a still further embodiment, $R^5$ represents trifluoromethyl. In a further embodiment, $R^5$ represents halo, such as chloro or fluoro. In a still further embodiment, $R^3$ represents chloro and $R^5$ represents chloro. In a further embodiment, $R^3$ represents fluoro and $R^5$ represents fluoro. In a still further embodiment, $R^3$ represents trifluoromethyl and $R^5$ represents trifluoromethyl.

In a special embodiment the compound of the invention is
N-(4-Chloro-3-trifluoromethyl-phenyl)-N'-[3-(1H-tetrazol-5-yl)-4'-trifluoromethyl-biphenyl -4-yl]-urea;
N-(3-Trifluoromethyl-phenyl)-N'-[4'-chloro-3-(1H-tetrazol-5-yl)-biphenyl-4-yl]-urea;
N-(4-Chloro-3-trifluoromethyl-phenyl)-N'-[4'-chloro-3-(1H-tetrazol-5-yl)-biphenyl-4-yl]-urea;
N-(3,5-Dichloro-phenyl)-N'-[4'-chloro-3-(1H-tetrazol-5-yl)-biphenyl-4-yl]-urea;
N-(3,5-Difluoro-phenyl)-N'-[4'-chloro-3-(1H-tetrazol-5-yl)-biphenyl-4-yl]-urea;
N-(3,5-Dichloro-phenyl)-N'-[3-(1H-tetrazol-5-yl)-4'-trifluoromethyl-biphenyl-4-yl]-urea;
N-(3,5-Difluoro-phenyl)-N'-[3-(1H-tetrazol-5-yl)-4'-trifluoromethyl-biphenyl-4-yl]-urea;
N-(3-Trifluoromethyl-phenyl)-N'-[4'-fluoro-3-(1H-tetrazol-5-yl)-biphenyl-5-yl]-urea;
N-(4-Chloro-3-trifluoromethyl-phenyl)-N'-[4'-fluoro-3-(1H-tetrazol-5-yl)-biphenyl-4-yl]-urea;
N-(3,5-Dichloro-phenyl)-N'-[4'-fluoro-3-(1H-tetrazol-5-yl)-biphenyl-4-yl]-urea;
N-(3,5-Difluoro-phenyl)-N'-[4'-fluoro-2-(1H-tetrazol-5-yl)-biphenyl-4-yl]-urea;
N-(4-Fluoro-3-trifluoromethyl-phenyl)-N'-[3-(1H-tetrazol-5-yl)-4'-trifluoromethyl-biphenyl-4-yl]-urea; N-(3,5-Bis-trifluoromethyl-phenyl)-N'-[3-(1H-tetrazol-5-yl)-4'-trifluoromethyl-biphenyl-4-yl]-urea;
N-(3,5-Bis-trifluoromethyl-phenyl)-N'-[4'-chloro-3-(1H-tetrazol-5-yl)-biphenyl-4-yl]-urea;
N-(4-Fluoro-3-trifluoromethyl-phenyl)-N'-[4'-chloro-3-(1H-tetrazol-5-yl)-biphenyl-4-yl]-urea;
N-(3,5-Bis-trifluoromethyl-phenyl)-N'-[4'-fluoro-3-(1H-tetrazol-5-yl)-biphenyl-4-yl]-urea;
N-(4-Fluoro-3-trifluoromethyl-phenyl)-N'-[4'-fluoro-3-(1H-tetrazol-5-yl)-biphenyl-4-yl]-urea;
N-(2-Trifluoromethyl-phenyl)-N'-[3-(1H-tetrazol-5-yl)-4'-trifluoromethyl-biphenyl-4-yl]-urea;
N-(2-Trifluoromethyl-phenyl)-N'-[4'-fluoro-3-(1H-tetrazol-5-yl)-biphenyl-4-yl]-urea;
N-(2-Bromo-phenyl)-N'-[3-(1H-tetrazol-5-yl)-4'-trifluoromethyl-biphenyl-4-yl]-urea;
N-(2-Trifluoromethyl-phenyl)-N'-[4'-chloro-3-(1H-tetrazol-5-yl)-biphenyl-4-yl]-urea;
N-(2-Bromo-phenyl)-N'-[4'-chloro-3-(1H-tetrazol-5-yl)-biphenyl-4-yl]-urea;
N-(2-Bromo-phenyl)-N'-[4'-fluoro-3-(1H-tetrazol-5-yl)-biphenyl-4-yl]-urea;
N-(2-Fluoro-phenyl)-N'-[3-(1H-tetrazol-5-yl)-4'-trifluoromethyl-biphenyl-4-yl]-urea;
N-(2-Fluoro-phenyl)-N'-[4'-chloro-3-(1H-tetrazol-5-yl)-biphenyl-4-yl]-urea;
N-(2-Fluoro-phenyl)-N'-[4'-fluoro-3-(1H-tetrazol-5-yl)-biphenyl-4-yl]-urea;
N-(2-Fluoro-phenyl)-N'-[4'-methyl-3-(1H-tetrazol-5-yl)-biphenyl-4-yl]-urea;
N-(2-Chloro-phenyl)-N'-[4'-methyl-3-(1H-tetrazol-5-yl)-biphenyl-4-yl]-urea;
N-(2-Bromo-phenyl)-N'-[4'-methyl-3-(1H-tetrazol-5-yl)-biphenyl-4-yl]-urea;
N-(2-Trifluoromethyl-phenyl)-N'-[4'-methyl-3-(1H-tetrazol-5-yl)-biphenyl-4-yl]-urea;
N-(2-Chloro-phenyl)-N-[3-(1H-tetrazol-5-yl)-4'-trifluoromethyl-biphenyl-4-yl]-urea;
N-(2-Chloro-phenyl)-N'-[4'-chloro-3-(H-tetrazol-5-yl)-biphenyl-4-yl]-urea;
N-(2-Chloro-phenyl)-N'-[4'-fluoro-3-(1H-tetrazol-5-yl)-biphenyl-4-yl]-urea;
N-(3,5-Dichloro-phenyl)-N'-[4'-methoxy-3-(1H-tetrazol-5-yl)-biphenyl-yl]-urea;
N-(3,5-Difluoro-phenyl)-N'-[3-(1H-tetrazol-5-yl)-4'-trifluoromethoxy-biphenyl-4-yl]-urea;
N-(3,5-Dichloro-phenyl)-N'-[3-(1H-tetrazol-5-yl)-4'-trifluoromethoxy-biphenyl-4-yl]-urea;
N-(3,5-Bis-trifluoromethyl-phenyl)-N'-[3-(1H-tetrazol-5-yl)-4'-trifluoromethoxy-biphenyl-4-yl]-urea;
N-(3,5-Difluoro-phenyl)-N-[3-(1H-tetrazol-5-yl)-3'-trifluoromethyl-biphenyl 4-yl]-urea;
N-(3,5-Dichloro-phenyl)-N'-[3-(1H-tetrazol-5-yl)-3'-trifluoromethyl-biphenyl-4-yl]-urea;
N-(3,5-Bis-trifluoromethyl-phenyl)-N'-[3-(1H-tetrazol-5-yl)-3'-trifluoromethyl-biphenyl-4-yl]-urea;
N-(3,5-Difluoro-phenyl)-N'-[4'-methoxy-3-(1H-tetrazol-5-yl)-biphenyl-4-yl]-urea;
N-(3,5-Bis-trifluoromethyl-phenyl)-N'-[4'-methoxy-3-(1H-tetrazol-5-yl)-biphenyl-4-yl]-urea;
N-(3-Bromo-phenyl)-N'-[3-(1H-tetrazol-5-yl)-4'-trifluoromethyl-biphenyl-4-yl]-urea;
N-(4-Chloro-phenyl)-N'-[3-(1H-tetrazol-5-yl)-4'-trifluoromethyl-biphenyl-4-yl]-urea;

N-(4-Fluoro-3-trifluoromethyl-phenyl)-N'-[3-(1H-tetrazol-5-yl)-3'-trifluoromethyl-biphenyl-4-yl]-urea;

or a pharmaceutically acceptable salt thereof.

Definition of Substituents

In the context of this invention halo represents fluoro, chloro, bromo or iodo.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Alkoxy is O-alkyl, wherein alkyl is as defined above.

Pharmaceutically Acceptable Salts

The chemical compound of the invention may be provided in any form suitable or the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric add, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic add, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic add, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred 'onium salts' include the alkyl-onium salts, the cycloalkyl-onium salts, and the cycloalkylalkyl-onium salts.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Pharmaceutical Compositions

In another aspect the invention provides novel pharmaceutical compositions comprising a therapeutically effective amount of a compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising a compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled In the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations Include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Ophthalmic Formulations

The pharmaceutical composition may be prepared in unit dosage forms suitable for topical ocular use. The therapeutically efficient amount typically is between 0.0001 and 5% (w/v), preferably between 0.001 and 1.0% (w/v) in liquid formulations.

For ophthalmic application, preferably solutions are prepared using a physiological saline solution as a major vehicle. The pH of such ophthalmic solutions should preferably be maintained between 4.5 and 8.0, more preferably between 6.5 and 7.2, with an appropriate buffer system. The formulations may also contain conventional, pharmaceutically acceptable preservatives, stabilizers and surfactants.

The preservative may be selected from hydrophobic or non-ionic preservatives, anionic preservatives, and cationic preservatives. Preferred preservatives that may be used in the pharmaceutical compositions of the present invention include, but are not limited to, benzalkonium chloride, chlorobutanol, thimerosal, phenylmercuric acetate and phenylmercuric nitrate.

A preferred surfactant is, for example, Polysorbate 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors, such as non-ionic tonicity adjustors, may be added as needed or convenient. They include, but are not limited to, salts, particularly sodium chloride, potassium chloride, mannitol and glycerol, polyethylene glycols (PEG), polypropylene glucols (PPG) or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

An ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

In the case of treating ophthalmic angiogenesis related diseases, disorders or conditions—such as AMD, the pharmaceutical composition of the invention may also be administered in the form of systemic administration (such as orally), as an eye ointment, or as an injection in the eye (periocular or intraocular injection).

Biological Activity

The compounds of the present invention are useful as blockers of chloride channels, such as Volume regulated anion channels (VRAC) or chloride channels of osteoclasts. For measuring the activity of the compounds, various chloride channel blocking assays known in the art can be used.

Methods of Therapy

Compounds that are active as chloride channels blockers are likely to be useful in the treatment of a number of diseases, disorders and conditions, including bone metabolic diseases, or diseases, disorders or conditions which are responsive to inhibition of angiogenesis.

Thus in a further aspect, the compounds of the invention are considered useful for the treatment, prevention or alleviation of a disease, disorder or condition responsive to the blockade of chloride channels.

In a special embodiment, the disease or a disorder or a condition is a bone metabolic disease, such as an osteoclast related bone disease. In a further embodiment, the disease or a disorder or a condition is an osteoclast related bone disease, such as osteoporosis, postmenopausal osteoporosis, secondary osteoporosis, osteolytic breast cancer bone metastasis, osteolytic cancer invation, and Paget's disease of bone.

The diseases, disorders or conditions that are responsive to inhibition of angiogenesis include but are not limited to:

diseases, disorders or conditions that involve the proliferation of tumor cells, such as cancer, prostate cancer, lung cancer, breast cancer, bladder cancer, renal cancer, colon cancer, gastric cancer, pancreatic cancer, ovarian cancer, melanoma, hepatoma, sarcoma and lymphoma;

ophthalmic angiogenesis related diseases, disorders or conditions, such as exudative macular degeneration, age-related macular degeneration (AMD), retinopathy, diabetic retinopathy, proliferative diabetic retinopathy, diabetic macular edema (DME), ischemic retinopathy (e.g. retinal vain or artery occlusion), retinopathy of prematurity, neovascular glaucoma, and corneal neovascularization; and rheumatoid arthritis, and psoriasis.

In a special embodiment, the disease, disorder or condition to be treated is a preneoplastic disease state. In a further embodiment, the treatment is an anti-metastatic treatment. In a still further embodiment, the disease, disorder or condition to be prevented is metastatic cancer.

In the context of this invention, "age-related macular degeneration" (AMD) includes dry AMD (non-exudative AMD) and wet AMD (exudative AMD). In a special embodiment, the invention relates to treatment, prevention or alleviation of wet AMD.

In a further embodiment, the disease or a disorder or a condition is sickle-cell anaemia.

Also, chloride channels blockers are likely to be useful in the treatment of a disease, disorder or condition that is responsive to reduction of intraocular pressure, such as ocular hypertension, open-angle glaucoma, chronic open-angle glaucoma, angle-closure glaucoma and ciliary injection caused by angle-closure glaucoma.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the dosis regimen may be reduced.

Combined Therapy

Use of the compounds of the invention may be combined with the use of other compounds useful for the treatment, prevention or alleviation of a disease, disorder or condition responsive to the blockade of chloride channels.

As an example, the compounds may be used in combination with one or more additional drugs useful for the treatment, prevention or alleviation of a disease responsive to inhibition of angiogenesis, such as compounds useful for anti-metastatic treatment. Such additional drugs include cytotoxic compounds, antimitotic compounds, and antimetabolites.

Examples of cytotoxic compounds (including cytotoxic alkylating agents) include carmustine (BCNU), fotemustin, temozolomide (temodal), ifosfamide, and cyclofosfamide.

Examples of antimitotic compounds include paclitaxel (taxol) and docetaxel.

An example of antimetabolites includes methotrexat.

Furthermore, the pharmaceutical composition for use according to the invention may be used or administered in combination with other treatments or therapies. Examples of other treatments or therapies include radiotherapy and surgery.

Also, use of the compounds of the invention may be combined with the use of other bone metabolism controlling compounds for the treatment of bone metabolic disease. Such known bone metabolism controlling compounds include bisphophonates such as etidronate, pamidronate, or clodronate optionally combined with calcium; oestrogen-receptor active compounds such as oestrogen i.e. oestradiol and ethyloestradiol, calcitonin, 1,25-dihydroxyvitamine D and metabolites thereof, fluoride, growth hormone, parathyroid hormone, trilodo-thyrosine, collagen degrading enzymes such as protease inhibitors, or cancer therapeutic agents.

Also, use of the compounds of the invention may be combined with the use of one or more additional drugs useful for the treatment, prevention or alleviation of a disease, disorder or condition is responsive to reduction of intraocular pressure. Such additional drugs include beta-blockers, parasympathomimetic miotics, sympathomimetics, and carbonic anhydrase inhibitors.

Furthermore, use of the compounds of the invention may be combined with other treatments or therapies.

The treatment of the diseases and disorder can be in chronical or a long term treatment as well as a treatment of sudden crisis in the disease and disorder.

EXAMPLES

The invention is further illustrated with reference to the following examples, which are not intended to be in any way limiting to the scope of the invention as claimed.

Example 1

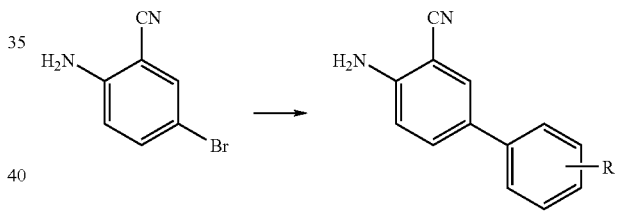

4-Amino-4'-trifluoromethyl-biphenyl-3-carbonitrile: To dimethoxyethane (100 mL) and water (50 mL) was added 2-amino-5-bromo-benzonitrile (8.1 g), 4-trifluoromethyl-phenyl-boronic acid (8.6 g) and potassium carbonate (18.7 g), nitrogen was bobbled through the mixture for 10 minutes. Under a nitrogen atmosphere was bis(triphenyl-phosphine) palladium (II) chloride (0.3 g) added, the reaction mixture was heated at reflux overnight, then cooled to room temperature and added water (150 mL). The mixture was extracted with ethyl acetate, the organic phase was washed with water (50 mL) and brine (50 mL), then dried with magnesium sulfate and evaporated to an oil. The product was purified by column chromatography. Yield 8.36 g of white powder.

Similarly was made:

4-Amino-4'-chloro-biphenyl-3-carbonitrile.

4-Amino-4'-fluoro-biphenyl-3-carbonitrile.

4-Amino-4'-methyl-biphenyl-3-carbonitrile.

4-Amino-4'-trifluoromethoxy-biphenyl-3-carbonitrile.

4-Amino-3'-trifluoromethyl-biphenyl-3-carbonitrile.

Example 2

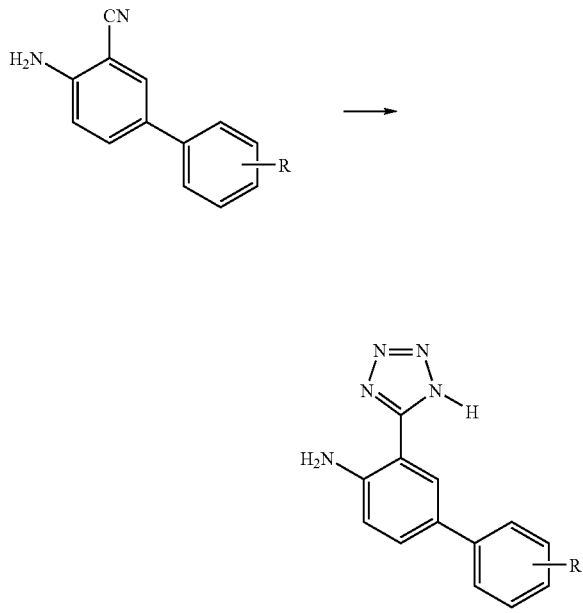

3-(1H-Tetrazol-5-yl)-4'-trifluoromethyl-biphenyl-4-ylamine: 4-Amino-4'-trifluoromethyl-biphenyl-3-carbonitrile (8.3 g) was dissolved in toluene (100 mL), to the solution was added sodium azide (3.1 g) and triethylammonium chloride (6.6 g). The reaction mixture was heated at 60-62° C. overnight, then cooled to room temperature and added water (40 mL), then hydrochloric acid (4 M, 13 mL) was added until pH=1. The product precipitated and was isolated by filtration, the precipitate was washed with cold water and dried on the filter by sucking air through the compound. Yield 10.2 g of white powder.

Similarly was made:
4'-Chloro-3-(1H-tetrazol-5-yl)-biphenyl-4-ylamine.
4'-Fluor-3-(1H-tetrazol-5-yl)-biphenyl-4-ylamine.
4'-Methyl-3-(1H-tetrazol-5-yl)-biphenyl-4-ylamine.
3-(1H-tetrazol-5-yl)-4'-trifluoromethoxy-biphenyl-4-ylamine.
3-(1H-tetrazol-5-yl)-3'-trifluoromethyl-biphenyl-4-ylamine.

Example 3

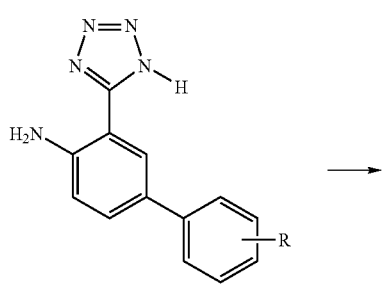

N-(4-Chloro-3-trifluoromethyl-phenyl)-N'-[3-(1H-tetrazol-5-yl)-4'-trifluoromethyl-biphenyl-4-yl]-urea: 3-(1H-Tetrazol-5-yl)-4'-trifluoromethyl-biphenyl-4-ylamine (0.5 g) and 4-choro-3-trifluoromethyl-phenyl isocyanate (0.4 g) in toluene (15 mL) was stirred at room temperature for two days. The reaction mixture was evaporated to an oil, the oil was dissolved in acetone and filtrated through Celite, the filtrate was added water, the product precipitated and was isolated by filtration. Yield 0.6 g Mp. 226-228° C.

Similarly was made:
N-(3-Trifluoromethyl-phenyl)-N'-[4'-chloro-3-(1H-tetrazol-5-yl)-biphenyl-4-yl]-urea: Mp. 253-254° C.
N-(4-Chloro-3-trifluoromethyl-phenyl)-N'-[4'-chloro-3-(1H-tetrazol-5-yl)-biphenyl-4-yl]-urea: Mp. 242-243° C.
N-(3,5-Dichloro-phenyl)-N'-[4'-chloro-3-(1H-tetrazol-5-yl)-biphenyl-4-yl]-urea: Mp. 231-234° C.
N-(3,5-Difluoro-phenyl)-N'-[4'-chloro-3-(1H-tetrazol-5-yl)-biphenyl-4-yl]-urea: Mp. 250-251° C.
N-(3,5-Dichloro-phenyl)-N'-[3-(1H-tetrazol-5-yl)-4'-trifluoromethyl-biphenyl-4-yl]-urea: Mp. 226-230° C.
N-(3,5-Difluoro-phenyl)-N'-[3-(1H-tetrazol-5-yl)-4'-trifluoromethyl-biphenyl-4-yl]-urea: Mp. 245-247° C.
N-(3-Trifluoromethyl-phenyl)-N'-[4'-fluoro-3-(1H-tetrazol-5-yl)-biphenyl-5-yl]-urea: Mp. 256-258° C.
N-(4-Chloro-3-trifluoromethyl-phenyl)-N'-[4'-fluoro-3-(1H-tetrazol-5-yl)-biphenyl-4-yl]-urea: Mp. 247-249° C.
N-(3,5-Dichloro-phenyl)-N'-[4'-fluoro-3-(1H-tetrazol-5-yl)-biphenyl-4-yl]-urea: Mp. 241-243° C.
N-(3,5-Difluoro-phenyl)-N'-[4'-fluoro-2-(1H-tetrazol-5-yl)-biphenyl-4-yl]-urea: Mp. 255-256° C.
N-(4-Fluoro-3-trifluoromethyl-phenyl)-N'-[3-(1H-tetrazol-5-yl)-4'-trifluoromethyl-biphenyl-4-yl]-urea: Mp. 247-249° C. (subl.).
N-(3,5-Bis-trifluoromethyl-phenyl)-N'-[3-(1H-tetrazol-5-yl)-4'-trifluoromethyl-biphenyl-4-yl]-urea: Mp. 246-248° C.
N-(3,5-Bis-trifluoromethyl-phenyl)-N'-[4'-chloro-3-(1H-tetrazol-5-yl)-biphenyl-4-yl]-urea: Mp. 230-233° C.
N-(4-Fluoro-3-trifluoromethyl-phenyl)-N'-[4'-chloro-3-(1H-tetrazol-5-yl)-biphenyl-4-yl]-urea: Mp. 243-245° C.
N-(3,5-Bis-trifluoromethyl-phenyl)-N'-[4'-fluoro-3-(1H-tetrazol-5-yl)-biphenyl-4-yl]-urea: Mp. 251-253° C.
N-(4-Fluoro-3-trifluoromethyl-phenyl)-N'-[4'-fluoro-3-(1H-tetrazol-5-yl)-biphenyl-4-yl]-urea: Mp. 253-254° C.
N-(2-Trifluoromethyl-phenyl)-N'-[3-(1H-tetrazol-5-yl)-4'-trifluoromethyl-biphenyl-4-yl]-urea: Mp. 240-243° C.
N-(2-Trifluoromethyl-phenyl)-N'-[4'-fluoro-3-(1H-tetrazol-5-yl)-biphenyl-4-yl]-urea: Mp. 256-258° C.
N-(2-Bromo-phenyl)-N'-[3-(1H-tetrazol-5-yl)-4'-trifluoromethyl-biphenyl-4-yl]-urea: Mp. 242-243° C.
N-(2-Trifluoromethyl-phenyl)-N'-[4'-chloro-3-(1H-tetrazol-5-yl)-biphenyl-4-yl]-urea: Mp. 290-292° C.

N-(2-Bromo-phenyl)-N'-[4'-chloro-3-(1H-tetrazol-5-yl)-biphenyl-4-yl]-urea: Mp. 255-256° C.

N-(2-Bromo-phenyl)-N'-[4'-fluoro-3-(1H-tetrazol-5-yl)-biphenyl-4-yl]-urea: Mp. 256-258° C.

N-(2-Fluoro-phenyl)-N'-[3-(1H-tetrazol-5-yl)-4'-trifluoromethyl-biphenyl-4-yl]-urea: Mp. 251-252° C.

N-(2-Fluoro-phenyl)-N'-[4'-chloro-3-(1H-tetrazol-5-yl)-biphenyl-4-yl]-urea: Mp. 257-259° C.

N-(2-Fluoro-phenyl)-N'-[4'-fluoro-3-(1H-tetrazol-5-yl)-biphenyl-4-yl]-urea: Mp. 263-264° C.

N-(2-Fluoro-phenyl)-N'-[4'-methyl-3-(1H-tetrazol-5-yl)-biphenyl-4-yl]-urea: Mp. 260-262° C.

N-(2-Chloro-phenyl)-N'-[4'-methyl-3-(1H-tetrazol-5-yl)-biphenyl-4-yl]-urea: Mp. 261-263° C.

N-(2-Bromo-phenyl)-N'-[4-methyl-3-(1H-tetrazol-5-yl)-biphenyl-4-yl]-urea: Mp. 255-257° C.

N-(2-Trifluoromethyl-phenyl)-N'-[4'-methyl-3-(1H-tetrazol-5-yl)-biphenyl-4-yl]-urea: Mp. 259-261° C.

N-(2-Chloro-phenyl)-N'-[3-(1H-tetrazol-5-yl)-4'-trifluoromethyl-biphenyl-4-yl]-urea: Mp. 254-255° C. (subl.).

N-(2-Chloro-phenyl)-N'-[4'-chloro-3-(1H-tetrazol-5-yl)-biphenyl-4-yl]-urea: Mp. 255-257° C. (subl.).

N-(2-Chloro-phenyl)-N'-[4'-fluoro-3-(1H-tetrazol-5-yl)-biphenyl-4-yl]-urea: Mp. 255-257° C. (subl.).

N-(3,5-Dichloro-phenyl)-N'-[4'-methoxy-3-(1H-tetrazol-5-yl)-biphenyl-4-yl]-urea: Mp. 200-201° C.

N-(3,5-Difluoro-phenyl)-N'-[3-(1H-tetrazol-5-yl)-4'-trifluoromethoxy-biphenyl-4-yl]-urea: Mp. 238-241° C.

N-(3,5-Dichloro-phenyl)-N'-[3-(1H-tetrazol-5-yl)-4'-trifluoromethoxy-biphenyl-4-yl]-urea: Mp. 224-225° C.

N-(3,5-Bis-trifluoromethyl-phenyl)-N'-[3-(1H-tetrazol-5-yl)-4'-trifluoromethoxy-biphenyl-4-yl]-urea: Mp. 238-240° C. (subl.).

N-(3,5-Difluoro-phenyl)-N'-[3-(1H-tetrazol-5-yl)-3'-trifluoromethyl-biphenyl-4-yl]-urea: Mp. 255-257° C.

N-(3,5-Dichloro-phenyl)-N'-[3-(1H-tetrazol-5-yl)-3-trifluoromethyl-biphenyl-4-yl]-urea: Mp. 236-239° C. (subl.).

N-(3,5-Bis-trifluoromethyl-phenyl)-N'-[3-(1H-tetrazol-5-yl)-3-trifluoromethyl-biphenyl-4-yl]-urea: Mp. 250-252° C.

N-(3,5-Difluoro-phenyl)-N'-[4'-methoxy-3-(1H-tetrazol-5-yl)-biphenyl-4-yl]-urea: Mp. 129-133° C.

N-(3,5-Bis-trifluoromethyl-phenyl)-N'-[4'-methoxy-3-(1H-tetrazol-5-yl)-biphenyl-4-yl]-urea: Mp. 219-221° C.

N-(3-Bromo-phenyl)-N'-[3-(1H-tetrazol-5-yl)-4-trifluoromethyl-biphenyl-4-yl]-urea: Mp. 203-210° C. (subl.).

N-(4-Chloro-phenyl)-N'-[3-(1H-tetrazol-5-yl)-4-trifluoromethyl-biphenyl-4-yl]-urea: Mp. 232-234° C.

N-(4-Fluoro-3-trifluoromethyl-phenyl)-N'-[3-(1H-tetrazol-5-yl)-3'-trifluoromethyl-biphenyl yl]-urea: Mp. 254-255° C.

The invention claimed is:

1. A chemical compound, which is:
   N-(3,5-Difluoro-phenyl)-N'-[3-(1H-tetrazol-5-yl)-3'-trifluoromethyl-biphenyl-4-yl]-urea;
   N-(3,5-Dichloro-phenyl)-N'-[3-(1H-tetrazol-5-yl)-3'-trifluoromethyl-biphenyl-4-yl]-urea;
   N-(3,5-Bis-trifluoromethyl-phenyl)-N'-[3-(1H-tetrazol-5-yl)-3'-trifluoromethyl-biphenyl-4-yl]-urea;
   or a pharmaceutically acceptable salt thereof.

2. A pharmaceutical composition comprising a therapeutically effective amount of a compound according to claim 1, or a pharmaceutically acceptable salt thereof, together with at least one pharmaceutically acceptable carrier, excipient or diluent.

3. The compound of claim 1, which is: N-(3,5-Difluoro-phenyl)-N'-[3-(1H-tetrazol-5-yl)-3'-trifluoromethyl-biphenyl-4-yl]-urea; or a pharmaceutically acceptable salt thereof.

4. The compound of claim 1, which is: N-(3,5-Dichloro-phenyl)-N'-[3-(1H-tetrazol-5-yl)-3'-trifluoromethyl-biphenyl-4-yl]-urea; or a pharmaceutically acceptable salt thereof.

5. The compound of claim 1, which is: N-(3,5-Bis-trifluoromethyl-phenyl)-N'-[3-(1H-tetrazol-5-yl)-3'-trifluoromethyl-biphenyl-4-yl]-urea; or a pharmaceutically acceptable salt thereof.

* * * * *